United States Patent [19]
Young

[11] Patent Number: 5,557,405
[45] Date of Patent: Sep. 17, 1996

[54] MEASUREMENT OF DROPLET SIZE IN A PHOTOGRAPHIC DISPERSION

[75] Inventor: David J. Young, Hertfordshire, United Kingdom

[73] Assignee: Eastman Kodak Company, Rochester, N.Y.

[21] Appl. No.: 556,347

[22] Filed: Nov. 13, 1995

Related U.S. Application Data

[63] Continuation of Ser. No. 284,329, Aug. 2, 1994, abandoned.
[51] Int. Cl.$^6$ .................................................. G01N 15/02
[52] U.S. Cl. ............................................ 356/336; 356/36
[58] Field of Search ................................. 356/335–343, 356/36, 440; 430/30; 523/333–335; 366/6, 144, 162.1

[56] References Cited

U.S. PATENT DOCUMENTS

| | | |
|---|---|---|
| 3,177,706 | 4/1965 | Shuman et al. . |
| 4,075,462 | 2/1978 | Rowe . |
| 4,181,009 | 1/1980 | Williamson ............................. 73/61.4 |
| 4,653,914 | 3/1987 | Watson ................................... 356/344 |
| 4,752,131 | 6/1988 | Eisenlauer et al. ..................... 356/338 |
| 4,779,003 | 10/1988 | Tatsuno ................................. 250/575 |
| 5,399,015 | 3/1995 | Zhi-qiang et al. ...................... 366/339 |

FOREIGN PATENT DOCUMENTS

| | | |
|---|---|---|
| 2071841 | 9/1981 | United Kingdom . |
| 2182432 | 5/1987 | United Kingdom . |

Primary Examiner—Hoa Q. Pham
Attorney, Agent, or Firm—Arthur H. Rosenstein

[57] ABSTRACT

In order to maintain product quality control and process control when producing photographic materials, it is necessary to measure droplet size of dispersions or dispersion melts utilized to produce such materials. Known methods of measuring the droplet size require off-line techniques and there is no readily available process control. Described herein is an on-line technique for the measuring of droplet size which provides such process control.

8 Claims, 3 Drawing Sheets

MEASUREMENT OF DROPLET SIZE IN A PHOTOGRAPHIC DISPERSION

This is a Continuation of application Ser. No. U.S. 08/284,329, filed 02 Aug. 1994, now abandoned.

FIELD OF THE INVENTION

The present invention relates to the measurement of droplet size in a photographic dispersion, and is more particularly concerned with carrying out such measurement when on-line.

1. Background of the Invention

In order to maintain product quality control and process control when producing photographic materials, it is necessary to measure droplet size of dispersions or dispersion melts utilized to produce such materials. This measurement of droplet size gives an indication of the efficiency of use of couplers in the dispersion or dispersion melts.

Such measurement is normally carried out using instruments such as turbidimetry analyzers, photon correlation spectrometers, and disc centrifuges. Techniques including sedimentation field flow fractionation (sfff) and optical and electron microscopy are also used.

2. Problem to be Solved by the Invention

When carrying out the measurement of dispersion droplet size using the apparatus and techniques mentioned above, a sample of the dispersion is removed from the product line for analysis. As this is time-consuming, only a relatively small number of samples are measured, and as a consequence, continuous control of the quality of the process and the product produced therefrom is not possible.

SUMMARY OF THE INVENTION

It is therefore an object of the present invention to provide a method of measuring droplet size of a photographic dispersion which can be carried out on-line.

In accordance with one aspect of the present invention, there is provided a method of measuring droplet size of a photographic dispersion during its manufacture, the method comprising the steps of:

diverting a portion of the main flow of the dispersion from the main flow path;

illuminating the flowing sample comprising the diverted portion;

measuring the light scattered by the flowing sample; and determining the droplet size of the dispersion from the measured scattered light.

ADVANTAGEOUS EFFECT OF THE INVENTION

The above method has the advantage that measurement of droplet size can be carried out on-line, and this measurement can be used for process control during production of the dispersion itself.

BRIEF DESCRIPTION OF THE DRAWINGS

For a better understanding of the present invention, reference will now be made, by way of example only, to the accompanying drawings in which.

DETAILED DESCRIPTION OF THE INVENTION

Figure 1:
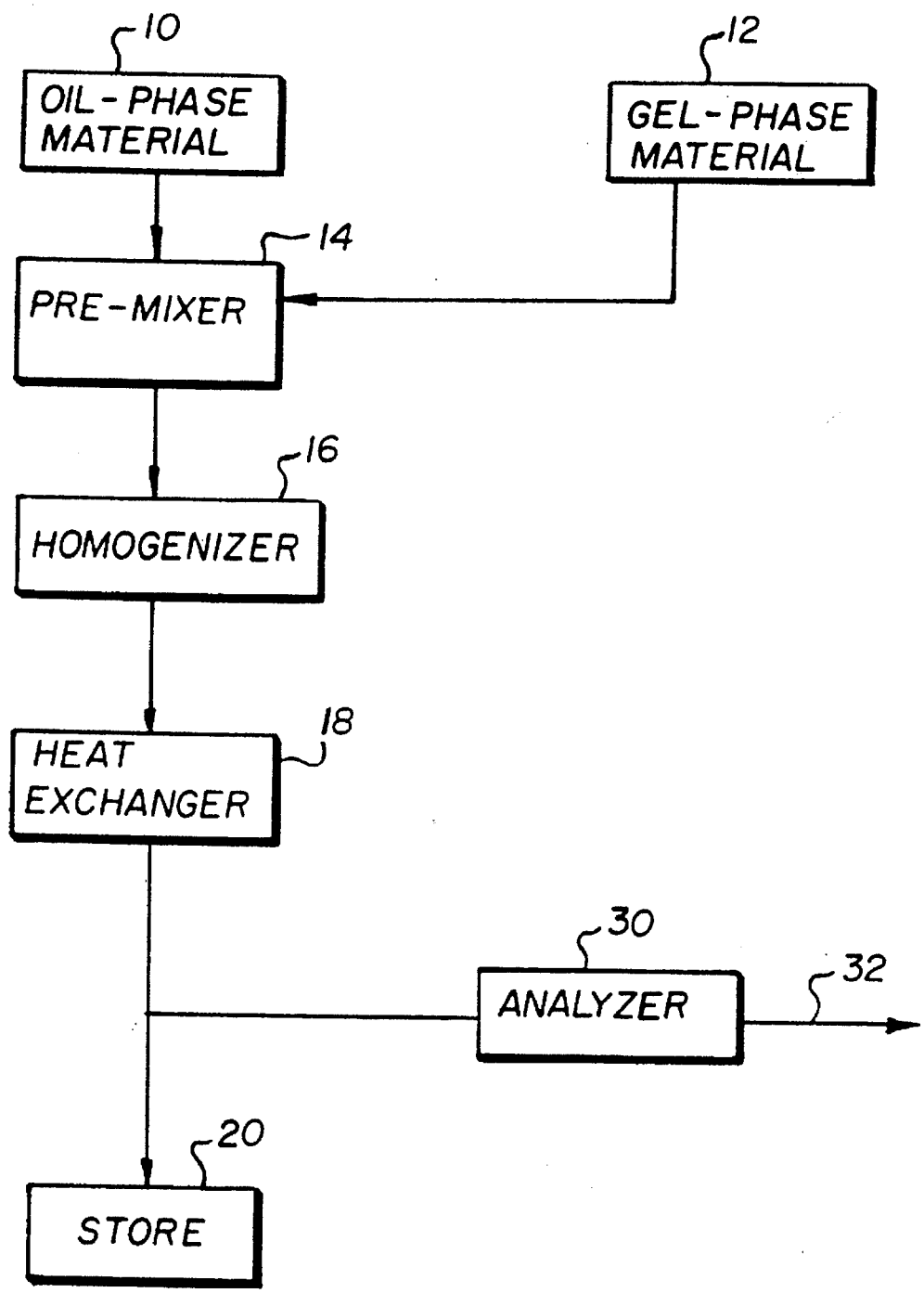
FIG. 1 is a flow chart illustrating some of the steps in the manufacture of a photographic dispersion.

FIG. 1 illustrates a flow chart of the steps in the manufacture of a photographic dispersion. The steps are as follows:

a) oil-phase materials 10 and gel-phase materials 12 are mixed in a pre-mixer 14;

b) the mixed material is passed to a homogenizer 16;

c) heat is removed from the mixed material in a heat exchanger 18; and d) the photographic dispersion produced is sent to store 20.

The method according to the present invention diverts part of the dispersion flow to an analyzer 30 which measures the droplet size in the photographic dispersion which has just been manufactured. An output signal 32 is produced which gives an indication of the droplet size.

Figure 2:
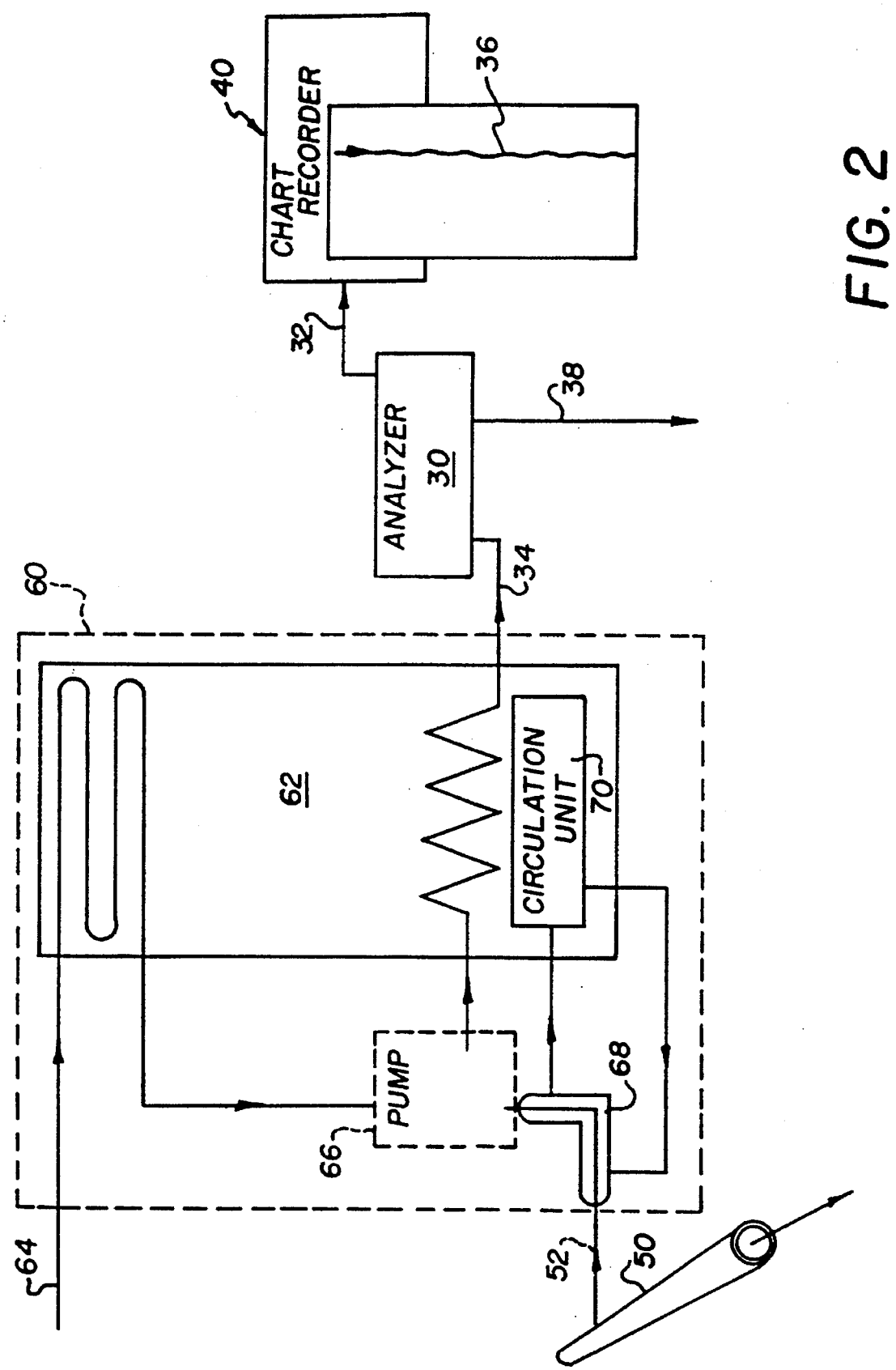
FIG. 2 is a schematic block diagram illustrating components of apparatus used to determine droplet size of a photographic dispersion.

In FIG. 2, apparatus for use in carrying out the method of the present invention is illustrated. The apparatus comprises an on-line analyzer 30 connected to receive a portion of the main dispersion flow for analysis at its flow input 34 and produces an output signal 32, as mentioned above, at its signal output 36 which can be recorded on a chart recorder 40. A flow output 38 is provided for the analyzed dispersion.

The main dispersion flow is shown generally at 50. A portion 52 of this flow is diverted and eventually enters the analyzer 30 at its flow input 34 after dilution.

Dilution of the portion 52 occurs in dilution unit 60 so that there is an appropriate ratio of water to dispersion in the range of 10:1 to 60:1 depending on the thickness of material at the point of analysis. Dilution is necessary because analyzer 30 requires an optimum dilution so that the maximum response can be provided. The exact ratio will depend on the dispersion being analyzed. In the arrangement to be described later, the dilution ratio is approximately 30:1.

The dilution unit 60 includes a constant temperature bath 62 which is maintained at a temperature in the range of 50° C. to 60° C. The dispersion has a tendency to set and needs to be kept in a liquid state to mix with the water and then to pass through the analyzer 30. A supply 64 of demineralised water passes through the bath 62 and, after attaining the desired temperature, it is connected to a double peristaltic pump 66.

The diverted dispersion flow 52 enters the dilution unit 60 into a double-walled pipe 68 which is connected to the pump 66. The outer section of the double-walled pipe 68 is also connected to a circulation unit 70 positioned in the bath 62. The circulation unit 70 allows the diverted dispersion flow 52 to attain the desired temperature before being passed through to the pump 66 where the dispersion 52 is combined with the demineralised water from supply 64 as mentioned above. This diluted flow forms the flow input 34 to the analyzer 30.

Figure 3:
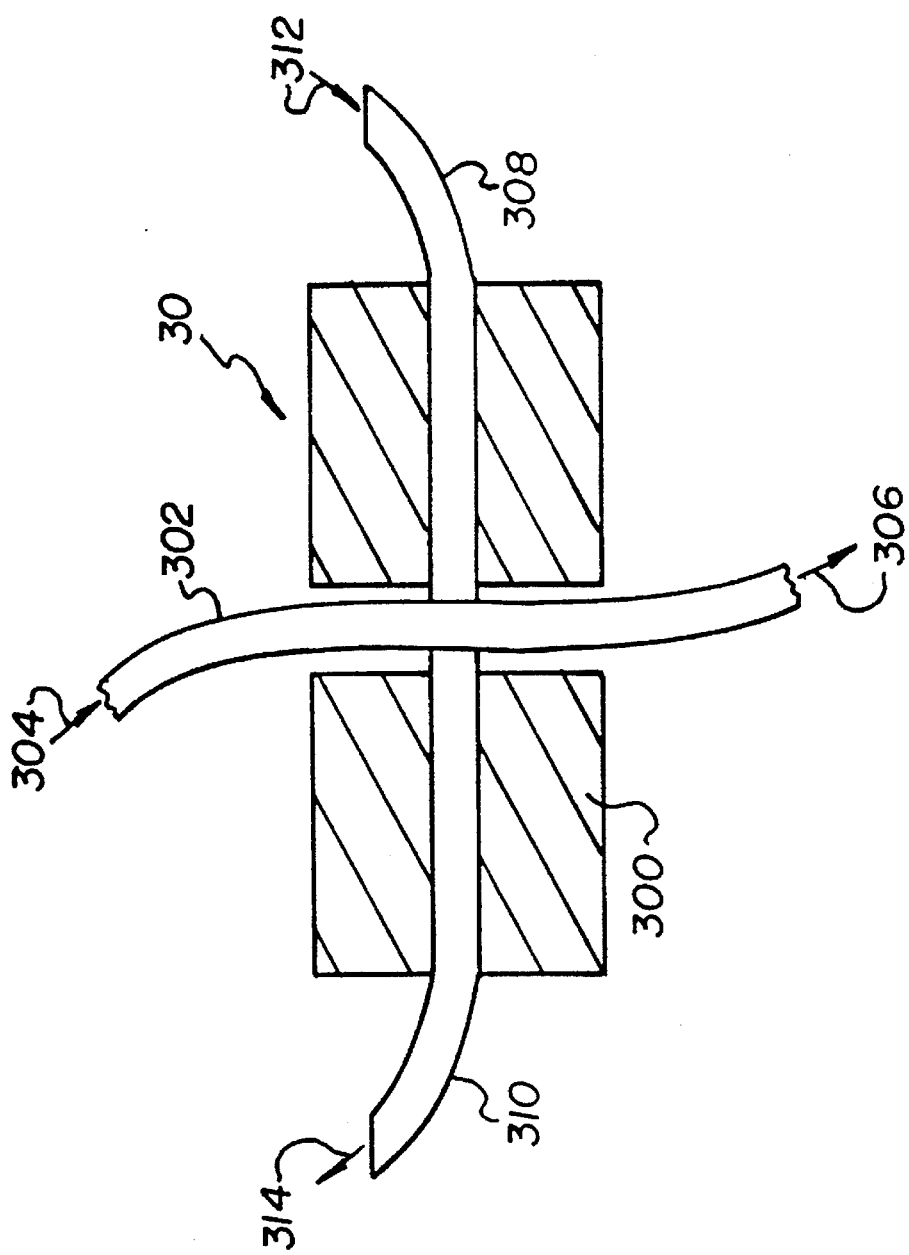
FIG. 3 is a schematic block diagram of an analyzer useful in the method according to the present invention.

The analyzer 30 is shown schematically in FIG. 3. It comprises a block 300 which houses transparent flexible tubing 302. The tubing 302 has an internal diameter of 1 mm. However, tubing having other internal diameters may be suitable according to the particular application.

The diluted dispersion to be analyzed enters the tubing 302 at 304 and leaves at 306. The block 300 also houses two fibre optic elements 308, 310. Element 308 is connected to a light source, for example, a high intensity infra-red light-emitting diode (not shown) at 312 and element 310 to a photodetector (also not shown) at 314. Element 310 collects the light transmitted through the tubing 302 and passes it to the photodetector for conversion to an output signal.

The flexible tubing 302 is slightly compressed (not shown) to provide a pair of parallel side walls which cuts down unwanted reflections at the tubing/diluted dispersion interfaces. Unwanted reflections are also cut down at the air/tubing interfaces as the tubing is pressed against the ends of elements 308 and 310.

The photodetector converts the light to a voltage which consists of a large dc component, which corresponds to the average transmitted light intensity, and a small fluctuating ac component due to the flowing droplets being illuminated in the tubing 302. The dc component is dependent of the mean turbidity of the dispersion. The root mean square (rms) value of the fluctuating ac component is related to the average number concentration and size of the droplets in the dispersion.

The rate of flow of the dispersion through the analyzer is controlled by pump 66 and lies in a range of 0.5 ml/min to 10 ml/min. However, a preferred range for the rate of flow is between 1 ml/min and 2 ml/min.

Apart from the major advantage of being able to continuously measure droplet size of a dispersion and to use that measurement to control the process producing the dispersion, the analyzer used is relatively inexpensive and easy to install. Furthermore, it is easy to operate in comparison to off-line techniques and apparatus mentioned above.

The method of the present invention could also be used for the on-line measurement and control of emulsions and melts at a range of position in the process.

Furthermore, entrained air bubbles or oily globules may also be detected on-line.

On-line warning of contamination of normally clear solutions in delivery lines can be detected using the method of the present invention. This is achieved by the detection of an increase in particulates or of a change in density.

I claim:

1. A method of manufacturing a photographic dispersion in a main flow path for subsequent use in manufacturing a photographic product, the method comprising the steps of:
   a) mixing together oil-phase materials and gel-phase materials in a mixing device to form a mixed oil-and gel-phase material;
   b) homogenizing the mixed oil- and gel-phase materials in a homogenizing device to form a homogenized photographic dispersion;
   c) removing heat from the mixed and homogenized photographic dispersion is a heat exchanging device;
   d) monitoring at least one property of the photographic dispersion produced, said at least one property of the photographic dispersion comprising droplet size; and
   e) storing the photographic dispersion until ready for use in manufacturing a photographic product;
   wherein step d) includes the steps of:
   (i) diverting a portion of the photographic dispersion from the main flow path to form a flowing sample;
   (ii) diluting the flowing sample with demineralized water to form a diluted flowing sample in accordance with a predetermined water to dispersion ratio;
   (iii) illuminating the diluted flowing sample with light from a light source, the diluted flowing sample scattering the illuminating light in accordance with said at least one property of the photographic dispersion;
   (iv) collecting the scattered light from the diluted flowing sample; and
   (v) analyzing the scattered light to provide an output signal indicative of said at least one property of the photographic dispersion.

2. Process control for the manufacture of photographic dispersions using a method according to claim 1.

3. A method according to claim 1, wherein said output signal comprises a voltage having a dc component and a fluctuating ac component, the dc component being dependent on turbidity of the diluted flowing sample of the photographic dispersion, and the ac component is related to concentration and size of droplets of the photographic dispersion.

4. A method according to claim 3, wherein said output signal is recorded on a chart recorder.

5. A method according to claim 1, wherein the diluted flowing sample has a flow rate in the range of 0.5 ml/min to 10 ml/min.

6. A method according to claim 5, wherein the flow rate is in the range of 1 ml/min to 2 ml/min.

7. A method according to claim 1, wherein the water to dispersion ratio lies in a range of approximately 10:1 to approximately 60:1.

8. A method according to claim 7, wherein the water to dispersion ratio is approximately 30:1.

\* \* \* \* \*